United States Patent [19]

Miles et al.

[11] Patent Number: 4,551,131
[45] Date of Patent: Nov. 5, 1985

[54] AUTOTRANSFUSION SYSTEM WITH ANTICOAGULANT DELIVERY SYSTEM

[75] Inventors: Clive Miles, Oakland; Gary Schneiderman, Walnut Creek, both of Calif.

[73] Assignee: Thoratec Laboratories Corporation, Berkeley, Calif.

[21] Appl. No.: 490,673

[22] Filed: May 2, 1983

[51] Int. Cl.⁴ .................... A61M 1/00; A61M 5/00
[52] U.S. Cl. .................................. 604/31; 604/35; 604/118; 604/269
[58] Field of Search .............. 604/902, 30, 35, 27, 604/82, 83, 246, 247, 408, 410, 403, 405, 269, 4–6, 31, 35, 65, 118–121; 137/545, 889, 891, 893, 896; 118/684

[56] References Cited

U.S. PATENT DOCUMENTS

| | | | |
|---|---|---|---|
| 3,799,702 | 3/1974 | Weishaar | 604/118 |
| 3,964,484 | 6/1976 | Reynolds et al. | 604/902 |
| 3,965,896 | 6/1976 | Swank | 604/83 |
| 4,395,258 | 7/1983 | Wang et al. | 604/119 |
| 4,466,804 | 8/1984 | Hmo | 604/4 |

OTHER PUBLICATIONS

Intraoperative Autotransfusion, Bennett, M. D., et al., Amer. Journal of Surgery, vol. 123, pp. 257–259.

Primary Examiner—C. Fred Rosenbaum
Assistant Examiner—J. L. Kruter
Attorney, Agent, or Firm—Flehr, Hohbach, Test, Albritton & Herbert

[57] ABSTRACT

A movable blood aspiration wand, especially for use in autotransfusion, carries with it a tank for anticoagulant replenished from an anticoagulant source fixed at a high source and is connected to a blood reservoir at a low elevation. Differences in wand height relative to the source and to the blood reservoir are compensated for, so that differences in wand height and corresponding blood and anticoagulant head do not substantially vary the anticoagulant proportion added to the aspirated blood.

34 Claims, 2 Drawing Figures

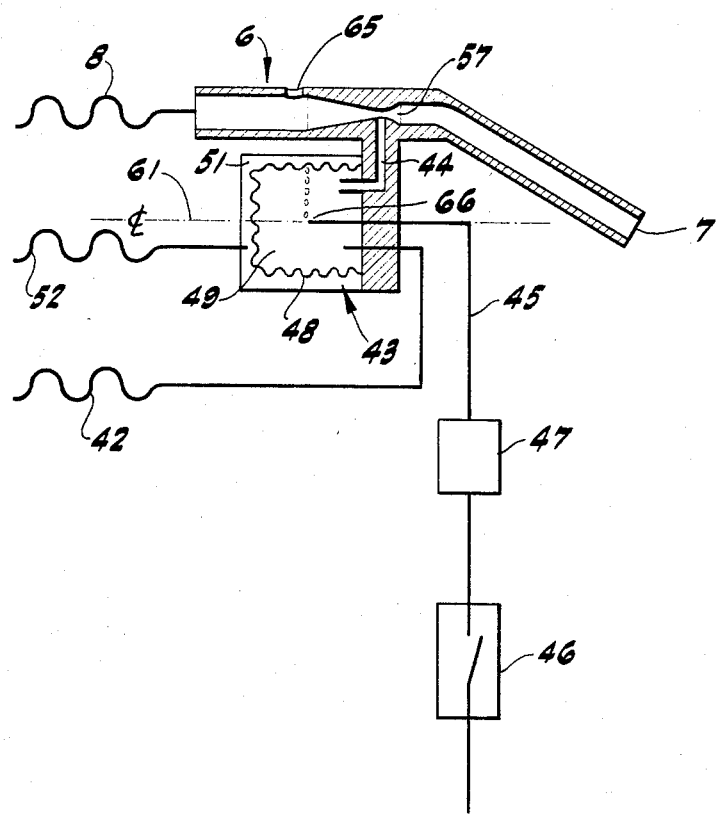

AUTOTRANSFUSION SYSTEM WITH ANTICOAGULANT DELIVERY SYSTEM

CROSS-REFERENCES TO RELATED APPLICATIONS

The application of Clive Miles entitled "Pressure Regulator" filed May 2, 1983 with Ser. No. 490,674 shows a vacuum regulator of the general kind disclosed herein, and the application of Robert H. Bartlett entitled "Autotransfusion System" filed Mar. 7, 1983 with Ser. No. 472,763 discloses a system having some similarities with the system disclosed herein for collecting, handling, and reinfusing autotransfused blood. The apparatus of the present disclosure includes a much improved anticoagulant delivery system.

BACKGROUND OF THE INVENTION

The invention relates to means for the use of an anticoagulant in connection with autotransfusion of blood. Customarily, an intraoperative autotransfusion system includes a suction wand for aspirating blood from an open wound site, a blood reservoir for collecting the aspirated blood, and a flexible conduit for conducting the blood from the wand to the reservoir. A known method of autotransfusion includes meeans for subjecting the interior of the blood reservoir to a source of vacuum effective through the flexible conduit for inducing blood to be aspirated into the wand and to flow from the wand, through the conduit into the reservoir. During handling of blood in an extracorporeal device such as an autotransfusion system, the blood readily tends to clot, and block the various structures through which it must flow, and thus may not be acceptable for reinfusion into the patient. Thus, it is often desirable to add an effective anticoagulant to the blood as, or promptly after, it is aspirated so that a mixture of blood and anticoagulant flows through the apparatus and may then be infused into the patient. The desirable proportion of anticoagulant to blood is generally fixed within a specific range. Anticoagulant can be added through a side port of the wand into a blood flow passageway or lumen where it mixes with the blood as it flows through the wand during aspiration. Commonly, a tube connects the site of anticoagulant entry at the wand with a source of anticoagulant positioned at a particular, generally fixed, height.

With such an anticoagulant delivery system, we have found that the delivery of anticoagulant to the blood flowing through the wand depends upon two key factors involving the height at which the wand is operated (i.e., the height of the wound site) relative: (1) to the height of the anticoagulant source; and (2) to the height of the blood inlet to the blood reservoir. This height sensitivity can be explained as follows. First, the driving force for anticoagulant delivery from the anticoagulant source to the blood flowing through the wand generally depends upon several factors, including the hydrostatic head of anticoagulant associated with the height difference between the anticoagulant source and the site of anticoagulant entry into the wand. Second, the flow rate of blood past the site of anticoagulant entry into the wand can affect the rate of anticoagulant delivery. The driving force for such blood flow from the wound site to the blood reservoir depends upon the sum of two pressures: the vacuum level within the blood reservoir; and the hydrostatic head of blood (within the line connecting the wand and the blood reservoir) associated with the height difference between the wand tip and the blood entry point into the blood reservoir. A variation in the hydrostatic pressure within the blood line can affect the flow rate of the blood, which in turn affects the driving force for anticoagulant flow into the wand.

Under a number of possible conditions, the height location of the wand at the aspiration site relative to both the blood reservoir and anticoagulant source can be variable. These conditions may include: inaccurate positioning during the initial set-up of the blood reservoir and/or anticoagulant source relative to the wound or blood aspiration site; and, after device set-up, a change in the wound site at which the wand is being used, or a repositioning of the patient. In any of these cases, the flow of anticoagulant into the wand for mixing with the blood in the above-described devices will tend to vary with the change in elevation of the wand relative to the anticoagulant source and blood reservoir, if they remain at fixed heights. This could alter the proportion of anticoagulant to the blood, and the desired range of said proportion may be exceeded.

The anticoagulant system described herein is particularly designed to compensate for the effects of changes in the aspirating wand elevation relative to the anticoagulant source and relative to the blood reservoir.

BRIEF SUMMARY OF THE INVENTION

The present structure is effective to maintain close to a set or predetermined value the proportion of anticoagulant added to aspirated blood, even though the blood aspirating wand elevation changes substantially. This is accomplished by utilizing two system design principles which combine to provide an anticoagulant delivery system which is virtually insensitive to the height of the wand relative to the height of the anticoagulant source and to the height of the blood inlet to the blood reservoir. First, a small holding tank for anticoagulant is mounted directly on, and "rides" with, the suction wand and communicates with the blood flow passageway or lumen of the suction wand through a small port. By design, the anticoagulant in this tank is maintained at (or near) atmospheric pressure and is automatically refilled through the line leading from a remote anticoagulant source or bottle. Thus, although the operating height of the suction wand relative to the main anticoagulant source reservoir may change with circumstance, anticoagulant at or near atmospheric pressure is always available to be drawn into the flowing blood in response predominantly to the hydrodynamic suction, created by the blood flow through the suction wand. Second, the system is designed to operate with a blood aspiration vacuum level within the blood reservoir which varies in direct response to changes in the operating height of the suction wand relative to the blood reservoir. Thus, starting with a selected operating vacuum level with the suction wand located at some arbitrary reference or datum height relative to the blood reservoir, the vacuum level available for blood aspiration is increased (pressure decreased) by one centimeter $H_2O$ (actually one centimeter of anticoagulant) for every centimeter that the suction wand may be used below the original datum position. Conversely, the vacuum level iss decreased (pressure increased) by one centimeter $H_2O$ (actually one centimeter of anticoagulant) for every centimeter that the suction wand may be used above the original reference or datum position. This tends to maintain the driving force for the aspirated blood approximately constant, and therefore the aspirated blood flow rate approximately constant. The combination results in an anticoagulant delivery system which is essentially free of "height effects" and which effectively meters anticoagulant delivery to the blood.

PRIOR ART OF INTEREST

U.S. Pat. Nos.

| | | | |
|---|---|---|---|
| 2,032,614 | Guiou | 3,719,197 | Pannier et al. |
| 2,449,497 | McLeod | 3,802,432 | Djerassi |
| 2,689,565 | Gobel | 3,807,401 | Riggle et al. |
| 2,697,435 | Ray | 3,853,126 | Schulte |
| 2,804,075 | Borden | 3,863,634 | Reynolds et al. |
| 2,935,068 | Donaldson | 3,866,608 | Reynolds et al. |
| 2,988,001 | D'Arcy et al. | 3,955,573 | Hansen et al. |
| 3,191,600 | Everett | 3,965,896 | Swank |
| 3,452,751 | Austin | 3,989,046 | Pannier et al. |
| 3,463,159 | Heimlich | 4,006,745 | Sorenson et al. |
| 3,492,991 | Dyer | 4,014,329 | Welch et al. |
| 3,595,234 | Jackson | 4,033,345 | Sorenson et al. |
| 3,623,483 | Dyer | 4,047,526 | Reynolds et al. |
| 3,680,560 | Pannier et al. | Re. 29,346 | Kopp |
| 3,704,709 | Sorenson et al. | | |

Publications:

Hematologic Integrity After Intraoperative Allotransfusion Aaron et al. Arch. Surg/Vol 108, June 1974

Intraoperative Autotransfusion Bennett et al. The American Journal of Surgery-Vol. 123, pgs, 257–260, 1972

Receptal ®ATS Mediastinal-4/78-S1390 Published by Sorenson Research Co. P. O. Box 15588, Salt Lake City, Utah Receptal ®ATS Trauma-1/79-S1220 Published by Sorenson Research Co. P. O. Box 15588, Salt Lake City, Utah A Simple Method of Intraoperative Autotransfusion Noon et al. Surgery, Gynecology and Obstetrics-Vol. 143, pgs. 65–70, 1976

The Graphic Languages of Engineering Steidel and Henderson John Wiley & Sons, 1983, Page 13, FIG. 1.7

BRIEF DESCRIPTION OF THE DRAWINGS

FIG. 2: An alternate configuration of the anticoagulant tank for affording a greater variety of wand orientations during use is shown.

DETAILED DESCRIPTION

Figure 1:
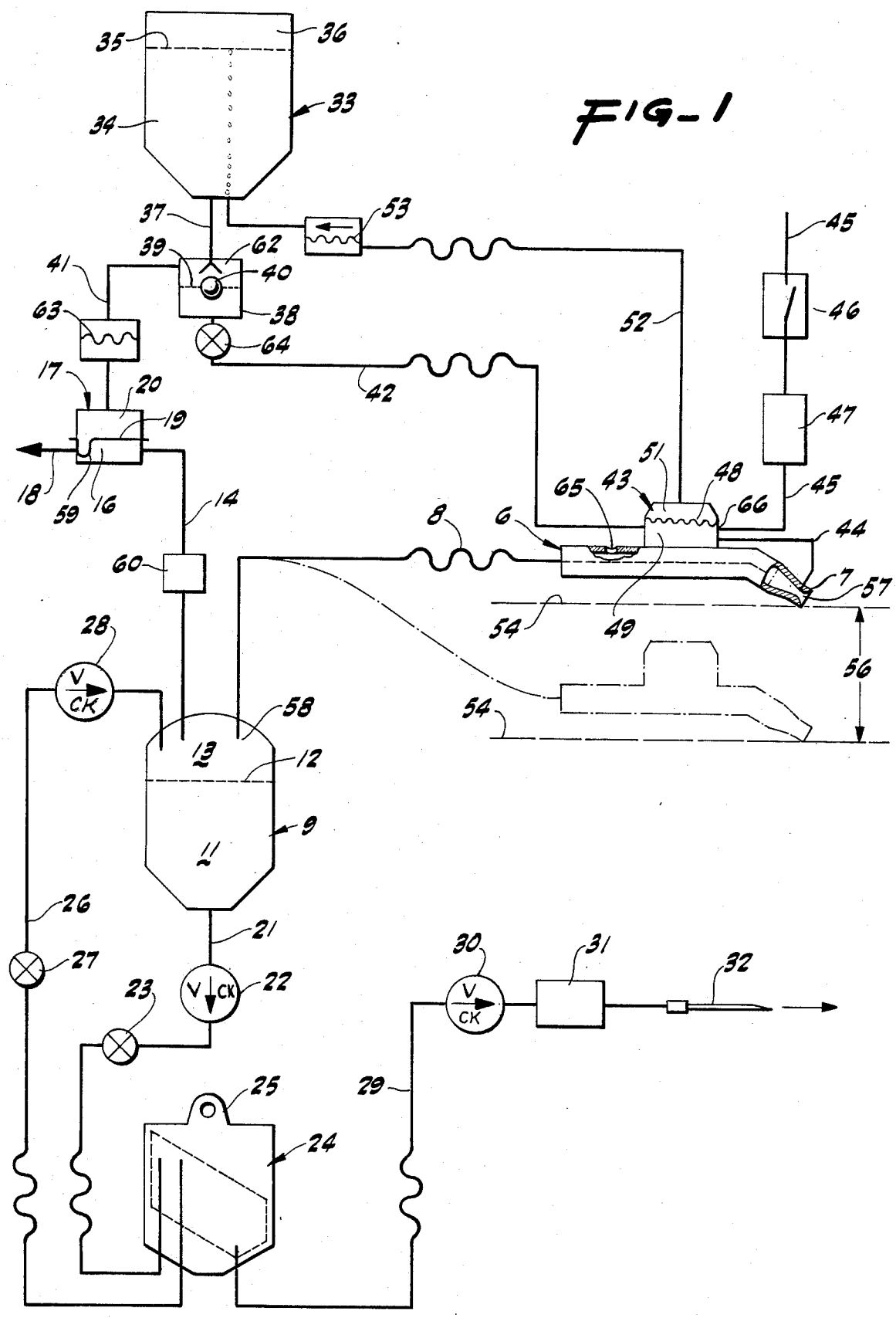
FIG. 1: An arrangement for adding anticoagulant to aspirated blood is shown, largely diagrammatically. Shown in the drawing is one preferred method for handling the anticoagulated blood for reinfusion into the patient, including one configuration of an anticoagulation tank.

The anticoagulant delivery system includes a movable, hand-held, hollow wand 6 having a tip or entrance opening 7. Preferably the interior of the wand includes a venturi shape 57 as indicated in the drawing. The exit opening of the wand is connected by a flexible conduit 8 to a rigid, generally closed blood reservoir 9 supported at a chosen elevation relative to the aspiration site. The reservoir 9 is adapted to receive a volume 11 of blood and anticoagulant, forming a surface 12 and leaving an upper space 13. Blood aspirated through the conduit 8 enters the space 13 at the conduit end 58. A tube 14 connects the space 13 to a suitable pressure regulator 17 for establishing vacuum within the space 13. The application of Clive Miles, entitled "Pressure Regulator", filed May 2, 1983, Ser. No. 490,674, discloses suitable pressure regulators using single or double diaphragm configurations. A single diaphragm configuration of the Miles-type is illustrated as pressure regulator 17. The tube 14 enters into a lower chamber 16 of the regulator 17. The lower chamber 16 is also joined to a source 18 of vacuum. The pressure regulator has a diaphragm 19 which partitions the regulator 17 into the lower chamber 16 and an upper regulator chamber 20. The diaphragm preferably has a peripheral flexible convolution 59. Pressure differences between the chambers 16 and 20 cause the diaphragm to move down or up. This diaphragm movement causes the convolution 59 to flex so as to move across and cover or uncover (depending upon whether the diaphragm is moving down, or up, respectively) more or less the opening of the tube 18 into the chamber 16. This action effects a pressure regulation in the chamber 16 according to the existing pressure in the chamber 20.

The lower end of the blood reservoir 9 has a flexible conduit 21 extending through a check valve 22 and a hand valve (or tubing clamp) 23 and leading into the upper part of the interior of a blood bag 24. This bag is of a flexible nature (as are standard blood bags) and has a supporting tab 25 for suspending the blood bag at either of two selected elevations described below. The dashed line in the figure indicates the outer sealed boundary of the blood bag interior. A flexible, blood bag de-airing duct 26, through a hand valve (or tubing clamp) 27 and a check valve 28, joins the upper interior of the blood bag 24 to the upper volume or space 13 of the blood reservoir 9. A flexible infusion tube 29 opens into the lower interior of the blood bag 24 and extends through a check valve 30 and a filter 31 to an infusion needle 32.

A rigid anticoagulant container 33, closed at the top, is supported at a predetermined elevation which is above the blood reservoir 9 and which must be above the highest usable position of the wand 6. The container 33 holds a charge 34 or supply of anticoagulant having a surface 35 and so leaving an unloaded space 36. As described below, the space 36 will normally be under subatmospheric pressure during use. A relatively small bore tube 37 joins the bottom of the container 33 to the upper portion of a drip housing 38 above a liquid level 39 therein. A floating ball valve 40, when lifted, blocks reverse flow through the drip tube 37 into the container 33.

The upper portion of the drip housing 38 is connected by a duct 41 to the upper chamber 20 of the pressure regulator 17. The lower part of the drip housing 38 is connected by a flexible conduit 42 or tube to an anticoagulant tank 43. A manual clamp or valve 64 may be used on the conduit 42. During use, the clamp or valve 64 is open. It is closed only for convenience during set-up or secondary operations involving refilling or replacement of the anticoagulant container 33. The tank 43 is fixedly supported on and is movable together with the wand 6 and may be of cylindrical form surrounding the wand. A hydrophobic membrane 48, permeable to air and impermeable to anticoagulant, divides the tank 43 into a mixed liquid (anticoagulant) and air chamber 49 and an air chamber 51. The chamber 49 of the anticoagulant tank 43 is joined by a pipe or passageway 44 to the interior passage of the wand 6 preferably at the throat of the venturi 57. An air conduit 45 leads from the atmosphere through a manually operated on/off valve 46 and a restricting orifice 47 into the chamber 49 of the tank 43. The chamber 51 is open to the bottom of the anticoagulant container 33 through a flexible tube 52 preferably having a flow device such as a hydrophobic membrane 53 or a check valve therein to limit or prevent liquid (anticoagulant) flow toward the tank 53.

In the customary use of the mechanism, a patient, lying on a bed or table, is supported at a particular elevation. An elevation 54 represents the location of the blood aspiration or wound site of the patient. The blood reservoir 9 is set up so that it is supported at a convenient height relative to 54. This position can, for example, be chosen somewhat arbitrarily such that the blood entry point 58 into the reservoir is approximately in line with the blood aspiration level 54. The container 33 is initially upright and filled with anticoagulant except for an air space at atmospheric pressure. The container is then connected to lines 37 and 52, and then inverted as shown in FIG. 1. The anticoagulant container 33 is then supported at a fixed, predetermined location above the blood entry point 58 into the reservoir. As described below, it is the vertical distance between the fluid surface 39 and the blood entry point 58 which sets the net driving force for blood aspiration from the wand tip 7 to the blood reservoir space 13. The positioning of the anticoagulant container 33 and blood reservoir 9 must be such that the liquid level 39 is somewhat above the uppermost point at which the wand 6 will be operated.

During initial priming, anticoagulant outflow by gravity is used to fill part of the drip housing 38 as well as the line 42, the chamber 49 and the line or pasageway 44. This outflow results in the establishment of a partial vacuum in the space 36 which is effective on the surface 35. During this priming, anticoagulant continues to flow out of the container 33 by gravity until the chamber 49 is completely full and until the vacuum level in the space 36 increases sufficiently to hold up the gravity head of the anticoagulant in the container 33, drip housing 38, line 42, and chamber 49. Using pressure units of centimeters H$_2$O (or, more precisely, centimeters of anticoagulant), the magnitude of the established vacuum in the space 36 is essentially numerically equal to the vertical distance in centimeters between the anticoagulant surface 35 and the anticoagulant/air interface at the entry point of the tube 45 into the chamber 49. Thus, the vacuum level in the space 36 will vary with different volumes of anticoagulant in the container 33 because the vertical location of the anticoagulant surface 35 will be different. However, as long as there is some anticoagulant remaining in the container 33, the vacuum level in a space 62 in the drip housing 38 will not vary with the anticoagulant level in the container 33, but will itself be numerically equal (in centimeters H$_2$O pressure) to the vertical distance in centimeters between the anticoagulant surface 39 and the anticoagulant/air interface at the entry point of the tube 45 into the chamber 49.

Since the upper chamber 20 of the regulator 17 is connected with the space 62 through the tube 41, the pressure in the chamber 20 substantially corresponds with said vacuum level in the space 62. If desired, a hydrophobic membrane 63 may be used in the line 41 to allow free air communication between the space 62 and the chamber 20, but prevent anticoagulant movement into the line 41. With vacuum available at the source 18, the regulator 17 acts (as described briefly above and in more detail in the above-referenced "Pressure Regulator" application of Clive Miles) to provide a regulated vacuum level in the space 13 of the blood reservoir 9.

As in conventional hand-held suction wands, an opening 65 may communicate the hollow interior or blood passageway of the wand 6 with the atmosphere. This opening may be shaped such that the use may conventionally cover the opening 65 with a finger to make the vacuum in the space 13 effective at the wand tip 7 to initiate and maintain blood aspiration, or remove his finger from the opening 65 to stop blood aspiration. With the opening 65 covered, the wand interior and entrance opening 7 are subject to vacuum from the source 18 acting through the regulator 17, the tube 14, the evacuated space 13 in the blood reservoir 9 and through the conduit 8. When not actually aspirating blood, atmospheric air will enter the wand through the opening 65 and/or the tip and flow through the system, being exhausted to the vacuum source 18. In this condition, the actual regulated pressure in the space 13 may be higher (less vacuum) than that in the chamber 20 because of vacuum degradation caused by air flow, rather than blood flow, into and through the wand.

In preparation for collecting blood, the manual valve 23 is preferably open, and the blood bag 24 is hung below the patient level at its lower of two positions.

In the remaining description of the autotransfusion system use, it is convenient to first describe the blood handling circuit and then the function of the anticoagulant circuit. The user grasps the wand 6 and maneuvers the tip 7 to aspirate blood shed by the patient. In doing so, the operator freely lifts and lowers the wand, as required, throughout a variable range 56 of altitudes or elevations above or below the altitude of the original plane 54. The solid-line and dotted-line outlines of the wand 6 are illustrative examples of such movement. With the appropriate configuration of the anticoagulant tank assembly 43 (as described below and illustrated in FIG. 2), the wand 6 may also be tipped or inclined or rotated or cocked in any practical fashion to facilitate induction of the patient's blood. When blood is to be aspirated, the on/off valve 46 must be open. When blood aspiration is stopped, the on/off valve 46 is preferably closed. The blood is induced by vacuum to flow through the inlet 7, through the wand including the venturi 57, and then from the exit of the wand 6 through the flexible conduit 8 into the blood reservoir 9 where it forms or joins a volume 11 of blood therein. As described below, anticoagulant automatically mixes with the aspirated blood as it flows through the wand.

From the blood reservoir 9, anticoagulated blood flows downwardly through the conduit 21 past the check valve 22 and the open valve 23 into the blood bag 24. Flow of blood may entrain air that travels with the blood to the blood bag 24. To assist in de-airing the blood bag, the conduit 21 opens into the top portion of the blood bag. Gravital separation of the blood and air tends to take place with the air occupying the upper portion of the blood bag. The interior shape of the blood bag (indicated by the dashed lines in FIG. 1) is contoured to assist rising air to travel toward the opening of the de-airing duct 26 and for contained blood to flow toward the opening of the tube 29. Manual manipulation of the blood bag may also be used to aid in the movement of air bubbles to the top of the bag. Prior to blood delivery to the patient, the air in the blood bag is preferably removed. The valve or clamp 23 is closed. From the upper part of the blood bag, collected air flows in a closed path through the de-airing duct 26, and the open valve or clamp 27 and the valve 28 therein, into the space 13 in the blood reservoir 9. The air may be induced to flow by manually squeezing the flexible blood bag 24 and by reason of the vacuum in the space 13. The closed-circuit de-airing path is not subject to external contamination. Also, any entrained blood cannot escape the system, but simply reenters the blood reservoir 9. After de-airing, the valve or clamp 27 is preferably closed.

As described in the above-referenced application of Robert H. Bartlett, entitled "Autotransfusion System", when the blood bag 24 is partly or entirely filled (and de-aired), it is lifted to an appropriate elevation above the patient so as to return his blood to him. Blood from the bag 24 flows through the tube 29 past the check valve 30 and the filter 31. Flow is then through the needle 32 into the patient for completion of the autotransfusion. Retrograde flow from the blood bag 24 into the blood reservoir 9 is prevented by the check valve 22. During blood delivery to the patient from the blood bag, hanging in its upper position above the patient, blood can still be aspirated and collected within the blood reservoir 9. When empty, the blood bag 24 is returned to its lower position for refilling from the blood reservoir 9 through the line 21. When in this filling position, which is generally of lower elevation than the patient, backflow of blood from the needle 32 toward the blood bag 24 is prevented by automatic closure of the check valve 30.

With respect to the anticoagulation process, as blood is aspirated through the lumen of the suction wand 6, including the venturi 57, a hydrodynamic suction is created by the flowing of the blood at the site of anticoagulant introduction into the blood from the tube 44. In response, anticoagulant is drawn into the wand lumen, where it mixes with the flowing blood. As the anticoagulant flows through 44 from the chambr 49, a decreased pressure draws air into the chamber from the atmosphere through the tube 45. All of this air subsequently passes through the hydrophobic membrane 48, which, by its nature, prohibits the like passage of anticoagulant. The passage of air across the membrane 48 may be facilitated by the partial vacuum on the air side of 48, which is associated with the vacuum in the space 36. The air passes through the tube 52 and into the container 33. The in-line device 53 prevents anticoagulant from entering into (or too far into) 52 from 33. The device 53 may be a hydrophobic membrane, as indicated in FIG. 1, or a check valve. Air entering the container 33 from 52 bubbles up through 34 to the space 36 at the closed end of 33. The air venting into the space 36 decreases the vacuum level (increases the pressure) in the space 36, allowing anticoagulant to flow through the tube 37 into the drip chamber 38, down the tube 42 and into the chamber 49, tending to refill the chamber. As long as anticoagulant continues to be drawn from the chamber 49, air continues to be drawn in through 45 and continues to be allowed to pass through the hydrophobic membrane 48, the vacuum in the space 36 will continue to be decreased, and anticoagulant will continue to flow from the container 33. However, if blood aspiration is ceased, anticoagulant will cease to be drawn from the chamber 49, air will not be drawn into the chamber 49 from the tube 45, and the chamber 49 will completely refill with anticoagulant. Under these conditions, the anticoagulant flow to the chamber 49 will be nearly stopped because the anticoagulant-side of the membrane 48 will be completely covered with anticoagulant. However, in practice, some small amount of anticoagulant may continue to flow until the vacuum level in the space 36 is reestablished to static conditions (i.e., until the vacuum level in the space 36 becomes large enough to offset the hydrostatic head of anticoagulant between the surface 35 and the location of the air inlet 45 in the chamber 49. In effect, the above-described apparatus provides a holding tank for anticoagulant (chamber 49) which: is mounted on, and moves with, the suction wand; maintains the anticoagulant in the tank at, or near, atmospheric pressure; and is automatically refilled with anticoagulant from a remote source (anticoagulant container 33). Thus, the wand may be operated at various vertical positions below the anticoagulant container or source without regard to the effects of a changing hydrostatic head of anticoagulant. In operation, the pressure in the chamber 49 may vary from its atmospheric value existing under static conditions due to the pressure drop generated by the air flow across the flow restrictor 47. The choice of the magnitude of restriction afforded by the restrictor 47 can be used as one design parameter for determining the actual proportion of anticoagulant and blood.

As described above, variations in the vertical distance between the wand tip 7 and the point 58 of blood entry into the blood reservoir 9 must also be addressed in providing a device designed to maintain adequate control over the proportion of anticoagulant added to the aspirated blood.

The anticoagulant line, including the chamber 49, the conduit 42, and the drip housing 38, constitute an enclosure for a liquid (anticoagulant) column which is effectively isolated or closed off from the atmosphere along its length or height and at its upper end. Because of the enclosed liquid column, lifting of the wand, for example, for operation from one elevation to a higher elevation causes a related decrease in vacuum (increase of pressure) within the drip housing 38. Conversely, lowering the wand for operation from an upper position to a lower elevation causes a related increase in vacuum (reduction of pressure) within the drip housing. The drip housing instantaneous pressure thus follows and corresponds to the momentary elevation of the wand.

These pressure changes are effective through the duct 41 upon the diaphragm 19 of the pressure regulator 17, which acts like a servo-mechanism. The diaphragm tends to provide a pressure in the chamber 16 which is equal to that in the chamber 20 by partially or completely uncovering or covering the end of the tube 18. The pressure in the space 13 is thus appropriately established at the proper amount to compensate for the greater or lesser height of the wand. Both the effective forces (vacuum and head or height) effecting flow through the wand 6 and the conduit 8 are varied inversely with respect to each other and so their sums remain substantially constant. The flow of blood through the nozzle 7 to the reservoir 9 is thus always subject to about the same impelling force and flows at about the same rate despite wand height changes.

Since the induction of anticoagulant into the wnd depends upon the rate of blood flow through the venturi entrance 7 and the rate of flow is almost invariable because of the controlling structure, the influx or aspiration of anticoagulant into the blood flow is also almost invariable with respect to changes in wand elevation relative to the blood reservoir. The proportion of anticoagulant added to the blood remains virtually the same despite changes in wand height.

As shown in FIG. 1, the structure of the anticoagulant tank cannot be operated with the wand 6 turned so that the chamber 49 is above the membrane 48, since air drawn into the chamber 49 from the line 45 will float up and away from the membrane 48. Air could not then reach the membrane 48 for passage therethrough until the chamber 49 became completely drained. In like manner, other orientations of the wand may result in improper performance of the system. To overcome this, the hydrophobic membrane separating the air and anticoagulant chambers of the tank may be contoured in a manner such that air readily meets the membrane surface for passage therethrough even though the wand may be held in a variety of acceptable positions. One such tank configuration is illustrated diagrammatically in FIG. 2, which is numbered in a corresponding way with FIG. 1. As in FIG. 1, the hydrophobic membrane 48 partitions the anticoagulant tank 43 into an air chamber 51 and an anticoagulant and air chamber 49. In FIG. 2, the general surface contour of the membrane 48 has the shape of a circular cylinder and includes an end cap. As shown, the membrane 48 is axis-symmetric about a centerline 61 with its end cap toward the exit of the wand 6. In this case, air drawn into the chamber 49 from the air line 45 will bubble up by its buoyancy, through the anticoagulant and will meet a site on the membrane 48 even though the wand 6 may be held in one of various orientations other than that shown in FIG. 2. For the particular configuration shown in FIG. 2, the only orientation in which the FIG. 2 device may not properly work is with the axis of symmetry 61 in a vertical direction and the hydrophobic membrane end cap of the membrane cylinder 48 at the lower end of the cylinder. This limitation of the FIG. 2 device is generally of limited or of no practical importance since blood will not be aspirated from below.

The above-described mechanism for compensating for changes in the wand elevation relative to the blood reservoir 9 is particularly effective when the wand tip 7 is maintained below the surface of a pool or blood and when predominantly blood rather than an air/blood mixture is being aspirated. For example, if the wand 6 is operated at an elevation below the blood reservoir port 58, the regulator 17 will automatically provide an increased vacuum level in the space 13 so as to compensate for the head of blood associated with the vertical distance between the port 58 and the entry port of air into the chamber 49 from the line 45. When the wand 6 is instead used at a blood-air interface, more or less air may be aspirated along with the blood. If significant amounts of air are aspirated along with the blood, the average density of fluid (blood plus air) in the blood line 8 will be lower than that if only blood were being aspirated. The regulated vacuum level in the space 13 may thus be somewhat higher than needed. However, this may be corrected somewhat by the proper choice of the value of an air flow restrictor 60 in the line 14. The air flow rate through the line 14 and through the regulator 17 will be greater under conditions of air/blood aspiration than under blood aspiration with no air. Thus, the pressure drop across the restrictor 60 will be greater in the case of blood/air aspiration, resulting in a higher pressure (lower vacuum) in the space 13. This tends to correct for the lower density of the blood/air mixture flowing through the line 8.

To maintain a proper proportion of anticoagulant and blood under various conditions of blood/air aspiration, it is also often helpful to: provide for a flow resistance for air flow into the chamber 49 from the line or tube 45; and/or provide for a threshold vacuum value in the chamber 49 (generally relatively small) below which air cannot flow into the chamber 49 from the line 45. The air flow restrictor 47 serves the former purpose. For the latter, the end 66 of the air line 45 may be positioned (as indicated in FIG. 2) in the anticoagulant in the chamber 49 beneath the anticoagulant at a selected depth, thus resulting in a selected hydrostatic head pressure of anticoagulant effective at the air tube end 66. The absolute value of the partial vacuum created in the chamber 49 by suction effective through the passage 44 must thus exceed the value of the hydrostatic pressure head effective on the tube end 66 within the chamber 49.

We claim:

1. An autotransfusion system with an anticoagulant delivery system comprising a wand having a flow passageway therethrough, said passageway having an inlet and an outlet, said wand adapted to be raised and lowered between different predetermined elevations above and below a reference elevation, means for continuously sensing the elevation level of said wand, means for moving liquid from said inlet to said outlet, means responsive to said sensing means for controlling said liquid moving means in accordance with the different elevations of said wand to afford a substantially predetermined movement of said liquid from said inlet to said outlet at said raised and lowered positions of said wand.

2. A system as in claim 1 in which said predetermined movement is independent of said wand elevations between said different predetermined elevations.

3. A system as in claim 1 in which said moving means includes means for establishing a vacuum, and said controlling means is effective to vary said vacuum.

4. A system as in claim 1 including an anticoagulant delivery system comprising an anticoagulant tank fixed on said wand, and means for admitting liquid from said anticoagulant tank into said passageway.

5. A system as in claim 4 in which said liquid in said anticoagulant tank is held at atmospheric pressure when blood is not being aspirated.

6. A system as in claim 4 in which said liquid in said anticoagulant tank is held at atmospheric pressure when blood is not being aspirated and said anticoagulant tank is automatically refilled.

7. An anticoagulant delivery system comprising a suction wand having a blood aspirating opening therein and adapted to move between different predetermined elevations above and below a reference elevation, a passageway through said wand for flow of aspirated blood therethrough, a blood reservoir, a tube for connecting said suction wand to discharge into said blood reservoir, a source of vacuum, means for subjecting said blood reservoir to a vacuum regulated from said vacuum source, means for continuously sensing the elevation of said wand and means responsive to said sensing means for correspondingly varying the magnitude of said vacuum in said blood reservoir.

8. A device as in claim 7 in which said means for subjecting said blood reservoir to a vacuum is a vacuum regulator, air conducting means connecting said vacuum regulator to said blood resevoir, and means in said air conducting means for restricting the air flow therethrough.

9. A device as in claim 8 comprising an anticoagulant delivery system, including an anticoagulant container at a fixed elevation above said blood reservoir, an anticoagulant tank fixed on and movable with said wand, a means for conducting anticoagulant from said container to said tank, and means for conducting anticoagulant from said tank into said blood flowing through said wand.

10. A device as in claim 9 comprising a drip tube chamber effectively closed to the atmosphere and disposed below said anticoagulant container, means for conducting anticoagulant from said anticoagulant container into the bottom of said drip tube chamber to leave a gas space in said chamber, means for conducting anticoagulant from said drip tube chamber to said passageway including a conduit closed to the atmosphere and open to the bottom of said drip tube chamber and open into said tank, and means responsive to pressure in said drip tube chamber for controlling said means for varying the amount of said vacuum.

11. A device as in claim 9 in which said blood flow passageway includes a venturi, and in which said anticoagulant is conducted from said tank into said blood at the location of said venturi.

12. A device as in claim 9 comprising means for transfusing blood into a patient at a particular elevation, a blood bag movable between an elevation below said blood reservoir elevation and an elevation above said patient elevation, first means for connecting said blood reservoir to said blood bag, and means for connecting said blood bag and said transfusing means.

13. A device as in claim 12 including second means for connecting said blood bag and said blood reservoir effective for de-airing said blood bag.

14. An anticoagulant delivery system comprising a suction wand having a blood aspirating opening and flow passageway therein and adapted to move between different elevations above and below a reference elevation, a tank mounted on and movable with said wand, a membrane permeable to air and impermeable to anticoagulant dividing said tank into an air chamber and an anticoagulant chamber, an anticoagulant container at a fixed elevation above said reference location and adapted to contain anticoagulant at the bottom thereof and having an enclosed space at the top thereof, means including a tube for conducting anticoagulant from said anticoagulant source to said anticoagulant chamber, means for conducting anticoagulant from said anticoagulant chamber into said blood flow passageway in said wand, means for admitting air to said anticoagulant chamber, and means for conducting air from said air chamber into said enclosed space of said anticoagulant source.

15. A device as in claim 14 in which said means for admitting air into said anticoagulant chamber requires an air pressure threshold to be exceeded for air passage therethrough.

16. A device as in claims 14 in which said means for admitting air into said anticoagulant chamber includes means for restricting the flow of said admitted air.

17. An autotransfusion system comprising a blood reservoir disposed at a particular elevation and having an upper portion and a lower portion, a movable suction wand adapted to receive blood, means for connecting said suction wand to discharge said blood into said blood reservoir, a blood bag having an upper portion and a lower portion, means for disposing said blood bag at an elevation below said blood reservoir, means for conducting blood and entrained air from said blood reservoir to said blood bag, and a closed conduit extending from said upper portion of said blood bag into said upper portion of said blood reservoir.

18. An anticoagulant delivery system comprising a suction wand having a blood aspirating opening and a blood flow passageway therein and adapted to move between a reference elevation and a higher elevation above said reference elevation and a lower elevation below said reference elevation, an anticoagulant container, a drip tube chamber closed to the atmosphere and disposed below said anticoagulant container and above said higher elevation of the wand, means connecting said anticoagulant container and said drip tube chamber, means including a tube for connecting said drip tube chamber to said blood flow passageway, means including a vacuum for inducing said aspirated blood to flow through said passageway of said wand, means for sensing the pressure in said drip tube chamber, and means responsive to said means for sensing pressure for varying the magnitude of said vacuum.

19. An anticoagulant delivery system comprising a suction wand having a fluid passage therein and adapted to move between a predetermined elevation above a reference elevation and a predetermined elevation below said reference elevation, a container adapted to contain an anticoagulant in the lower portion thereof and leaving a space above said anticoagulant, means for conducting anticoagulant from the lower portion of said container to said wand, means for continuously sensing the fluid pressure at a predetermined location along said anticoagulant conducting means and means for subjecting said fluid flowing through said passage of said wand to a subatmospheric pressure varying in accordance with changes of said fluid pressure at said predetermined location.

20. An anticoagulant delivery system comprising a movable wand having a passageway for aspirating blood therethrough, an anticoagulant container, said wand adapted to be operated between two different predetermined elevations relative to said container, a tank for anticoagulant connected to move with said movable wand, means connecting said anticoagulant tank with said passageway, means for automatically refilling said anticoagulant tank from said anticoagulant container and means for establishing the pressure within said anticoagulant tank substantially at atmospheric pressure independent of the position of said wand between said two predetermined elevations.

21. A device as in claim 17 including means for admitting air to a part of said anticoagulant tanks as said anticoagulant flows from said tank for mixing with said blood flowing through said passageway, connecting means which allows said admitted air to flow from said tank to said anticoagulant container, connecting means for conducting anticoagulant from said anticoagulant container to said anticoagulant tank, and means for releasing anticoagulant for flowing through said anticoagulant conducting means from said container to said tank in response to said air flow to said container.

22. A device as in claim 20 in which said pressure is substantially atmospheric.

23. A device as in claim 22 comprising means for sensing the elevation of said wand relative to said container.

24. A device as in claim 23 in which said sensing means includes a fluid-filled line.

25. A device as in claim 20 including a blood reservoir, means for conducting said aspirated blood from said wand to said blood reservoir, means for inducing said blood to flow into said wand and to said blood reservoir, and means for varying the magnitude of said flow inducing means in accordance with changes in the operating elevation of the wand relative to the elevation of the blood reservoir.

26. A device as in claim 25 in which said blood flow inducing means includes a vacuum.

27. A device as in claim 20 in which said wand passageway includes a venturi-type element and in which said anticoagulant connecting means connects said anticoagulant tank with said wand passageway in the vicinity of said venturi element.

28. A device as in claims 4, 9, 12 or 20 in which said anticoagulant tank is divided into a first chamber for air and a second chamber for anticoagulant by a membrane.

29. A device as in claim 28 in which said membrane is contoured to provide a surface effective to permit said air admitted into said second chamber to readily reach said membrane in a variety of operating orientations of said wand.

30. A device as in claim 29 in which said contour of said membrane is substantially cylindrical and which includes a cap on one end of said cylindrical contour.

31. An anticoagulant delivery system comprising a movable wand having a passageway for aspirating blood therethrough, said wand adapted to be operated at different elevations relative to a reference elevation, an anticoagulant tank connected to move with said movable wand, said anticoagulant tank beng in continuously open communication with said passageway, and means effective at any of said different elevations for establishing the pressure within said anticoagulant tank at atmospheric level when blood is not being aspirated through said passageway.

32. An anticoagulant delivery system as defined in claim 31 together with an anticoagulant container at said reference location, means connecting said anticoagulant container to said tank, and means for automatically refilling said anticoagulant tank from said anticoagulant container as anticoagulant is transferred from said tank to said passageway.

33. An anticoagulant delivery system as defined in claim 32 wherein said means for automatically refilling said anticoagulant tank from said anticoagulant container includes means for automatically delivering atmospheric air to said anticoagulant container as anticoagulant is transferred from said anticoagulant tank to the passageway of said wand.

34. An anticoagulant delivery system as in claim 33 together with means for restricting the delivery of atmospheric air.

* * * * *